United States Patent [19]

Fankhauser et al.

[11] Patent Number: 4,459,152
[45] Date of Patent: Jul. 10, 1984

[54] NITROARYLALKYLSULFONE DERIVATIVES AS PLANT GROWTH STIMULANTS

[75] Inventors: Ernst Fankhauser, Estavayer-le-Lac; Elmar Sturm, Aesch, both of Switzerland

[73] Assignee: Ciba-Geigy Corporation, Ardsley, N.Y.

[21] Appl. No.: 365,684

[22] Filed: Apr. 5, 1982

[30] Foreign Application Priority Data

Apr. 14, 1981 [CH] Switzerland ............... 2478/81

[51] Int. Cl.³ .................. A01N 41/10; A01N 43/08
[52] U.S. Cl. ................................. 71/103; 71/88; 568/30; 260/465 R; 47/DIG. 1
[58] Field of Search ......................... 71/103, 88

[56] References Cited

U.S. PATENT DOCUMENTS 3,802,863  4/1974  Walworth et al. ............. 71/103
4,086,079  4/1978  Otten et al. ................. 71/103

*Primary Examiner*—Catherine L. Mills
*Attorney, Agent, or Firm*—Frederick H. Rabin

[57] ABSTRACT

The invention describes gametocidal and microbicidal compositions which contain, as active ingredient, a nitroarylalkylsulfone derivative of the formula I

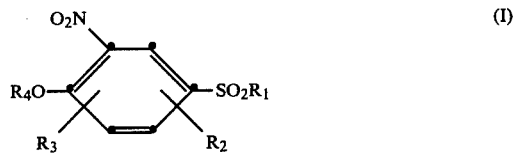

wherein $R_1$ is alkyl, $R_2$ and $R_3$ are each hydrogen, alkyl, alkoxy, haloalkyl, halogen, cyano, nitro or amino or together they complete a naphthalene ring; $R_4$ is hydrogen or $-COR_5$, wherein $R_5$ is alkyl, alkoxy, haloalkoxy, alkenyl, haloalkenyl, alkynyl, cycloalkyl, phenyl, benzyl, furyl or tetrahydrofuryl. The invention relates also to the use of these compositions and compounds for stimulating generative plant growth and for obtaining hybrid seeds, as well as to a method of preparing the hydrazinium and ammonium salts within the scope of the formula I, and to a process for preparing agrochemical compositions which contain compounds of the formula I as active ingredient.

18 Claims, No Drawings

NITROARYLALKYLSULFONE DERIVATIVES AS PLANT GROWTH STIMULANTS

The present invention relates to gametocidal and microbicidal compositions which contain, as active ingredient, a nitroarylalkylsulfone derivative of the formula I as defined below. The invention also relates to the use of said compositions and of the active ingredients contained therein for stimulating generative plant growth, in particular to the use thereof for producing male-sterile plants (use as gametocides). The invention further relates to the use of nitroarylalkylsulfone derivatives for regulating flower formation and the secondary effects associated therewith. In addition, the invention relates to a process for obtaining hybrid seeds and the nitroarylalkylsulfone derivatives themselves, where these are hydrazinium or ammonium salts. Finally, the invention also relates to the production of these salts and to the preparation of agrochemical compositions which contain the compounds of the formula I.

Nitroarylalkylsulfone derivatives within the scope of the present invention are compounds of the formula I

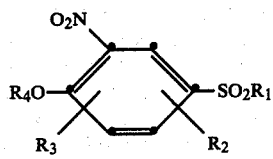
(I)

wherein
$R_1$ is $C_1$-$C_6$alkyl, $R_2$ and $R_3$, each independently of the other, are hydrogen, $C_1$-$C_6$alkyl, $C_1$-$C_6$alkoxy, $C_1$-$C_6$haloalkyl, halogen, cyano nitro or amino, or both together in the ortho-position to each other as a —(CH=CH)$_2$— group complete a naphthalene ring, $R_4$ is hydrogen, a cation or the —COR$_5$ group, wherein $R_5$ is $C_1$-$C_{12}$alkyl, $C_1$-$C_{12}$alkoxy, $C_1$-$C_{12}$haloalkoxy, $C_2$-$C_{10}$-alkenyl, $C_2$-$C_{10}$haloalkenyl, $C_2$-$C_6$alkynyl, $C_3$-$C_7$cycloalkyl, phenyl, benzyl, furyl or tetrahydrofuryl, and wherein each of the cyclic substituents is unsubstituted or mono- or polysubstituted by the same or different substituents selected from the group consisting of $C_1$-$C_3$alkyl, $C_1$-$C_3$alkoxy, $C_1$-$C_3$haloalkyl, halogen, cyano and nitro.

Depending on the indicated number of carbon atoms, alkyl by itself or as moiety of another substituent comprises e.g. the following groups: methyl, ethyl, propyl, butyl, pentyl, hexyl, heptyl, octyl, nonyl, decyl, undecyl or dodecyl, and the isomers thereof, e.g. isopropyl, isobutyl, tert-butyl, isopentyl etc. Alkenyl is e.g. vinyl, propen-1-yl, allyl, buten-1-yl, buten-2-yl, buten-3-yl etc., as well as chains containing several double bonds. Alkynyl is e.g. propyn-1-yl, propargyl, butyn-1-yl, butyn-2-yl etc., with propargyl being preferred. Haloalkyl is a mono- to perhalogenated alkyl substituent, e.g. CHCl$_2$, CH$_2$Cl, CCl$_3$, CCF$_3$, CH$_2$CH$_2$Cl etc. Throughout this specification, halogen denotes fluorine, chlorine, bromine or iodine, with chlorine and bromine being preferred. Cycloalkyl is e.g. cyclopropyl, cyclobutyl, cyclopentyl, cyclohexyl or cycloheptyl, with cyclopentyl and cyclohexyl being preferred. Haloalkenyl and haloalkyl are respectively an alkenyl and an alkoxy group, each monosubstituted or polysubstituted by halogen, preferred halogens being chlorine and bromine, most preferably chlorine. Lower alkyl will here always be understood as meaning $C_1$-$C_8$alkyl.

A cation will be understood as meaning e.g. the inorganic cation of an element of the first to fourth main group of the Periodic Table. Typical representatives are the alkali metals such as lithium, sodium or potassium, or the alkaline earth metals such as magnesium, calcium, barium or elements such as aluminium, tin or lead. A cation is also the cation of an element of the first to eighth auxiliary group, e.g. chromium, manganese, iron, cobalt, nickel, copper, zinc, silver or mercury. Preferred cations are alkali metal cations and alkaline earth metal cations as well as the cations of the elements of the third and fourth group of the Periodic Table. Depending on the valency of the metal cation, the compounds of the formula I contain one or more phenolate radicals. The term "cation" also denotes organic cations such as ammonium ions or hydrazinium ions. The ammonium and hydrazinium salts of the formula I are novel, highly active, and constitute a particularly preferred embodiment of this invention.

Examples of suitable ammonium ions are: NH$_4$, NH(alkyl)$_3$, NH$_2$(alkyl)$_2$ and NH$_3$(alkyl), such as NH(CH$_3$)$_3$, NH(C$_2$H$_5$)$_3$, NH$_2$(CH$_3$)$_2$, NH$_2$(C$_3$H$_7$-n)$_2$, NH$_3$CH$_3$, NH$_3$C$_4$H$_9$-n, or quaternary ammonium ions such as tetraethylammonium, tetrapropylammonium, tetrabutylammonium, tetrapentylammonium, tetrahexylammonium, tetraheptylammonium, tetraoctylammonium, tetranonylammonium, tetradecylammonium, methyltributylammonium, dimethyldibutylammonium, trimethylbutylammonium, methyltrioctylammonium, benzyltrimethylammonium, benzyltriethylammonium, benzyltripropylammonium, benzyltributylammonium, benzyldimethylhexadecylammonium, benzyldiethylhexadecylammonium, diisobutylcresoxyethyldimethylbenzylammonium, trimethylphenylammonium, diphenyldimethylammonium, butyltripropylammonium, tributylphenylammonium or tricaprylmethylammonium. Suitable hydrazinium ions are unsubstituted or substituted hydrazinium ions, such as NH$_2$NH$_3$, NH$_2$N(alkyl)$_3$, NH$_2$NH(alkyl)$_2$, NH$_2$NH$_2$(alkyl) etc.

In addition to NH$_4$, preferred ammonium cations comprise, in particular, those of the type NH$_{(4-a)}$(-lower alkyl)$_a{}^+$, in which a=1, 2, 3, or 4, and among these, in particular tetraalkylammonium ions such as N(CH$_3$)$_4{}^+$, N(C$_2$H$_5$)$_4{}^+$, N(C$_4$H$_9{-n}$)$_4{}^+$, N(CH$_3$)$_2$(C$_2$H$_5$)$_2{}^+$, N(C$_3$H$_7{-n}$)$_4{}^+$, N(C$_3$H$_7{-i}$)$_4{}^+$ etc.

The compounds of formula I are oils, resins or mainly solids which are stable at room temperature and have very valuable microbicidal and plant growth regulating properties. They may therefore preferably be used in agriculture or related fields for selectively influencing flower formation in plants and are also suitable for controlling phytopathogenic microorganisms.

A preferred group of compounds comprises compounds of the formula I, wherein $R_1$ is $C_1$-$C_3$alkyl, $R_2$ and $R_3$, each independently of the other, are hydrogen, $C_1$-$C_3$alkyl, $C_1$-$C_3$alkoxy, $C_1$-$C_3$haloalkyl, halogen, cyano, nitro or amino, or both together in the ortho-position to each other as —(CH=CH)$_2$-group complete a naphthalene ring; $R_4$ is hydrogen, an alkali metal cation or alkaline earth metal cation or the —COR$_5$ group, wherein $R_5$ is $C_1$-$C_6$alkyl, $C_1$-$C_6$alkoxy, $C_1$-$C_6$haloalkoxy, $C_2$-$C_5$alkenyl, $C_2$-$C_5$haloalkenyl, $C_2$-$C_5$alkynyl, $C_3$-$C_7$cycloalkyl, phenyl, benzyl, furyl or tetrahydrofuryl, and wherein each of the cyclic substituents is unsubstituted or substituted by identical or different substituents selected from the group consisting of methyl, ethyl, methoxy, ethoxy, halomethyl, fluorine, chlorine, bromine, cyano and nitro. Whithin this group of compounds, those compounds are particularly preferred in which the total number of carbon atoms in the substituents $R_1$, $R_2$, $R_3$ and $R_4$ does not exceed 8.

Preferred compounds are also those of the formula I, wherein $R_1$ is methyl or ethyl, $R_2$ is hydrogen, $R_3$ is hydrogen, methyl, methoxy, trifluoromethyl, bromine, cyano, nitro or amino, $R_4$ is hydrogen, or the —$COR_5$ group, wherein $R_5$ is $C_1$–$C_3$alkyl, $C_1$–$C_3$alkoxy, $C_1$–$C_3$haloalkoxy, $C_2$–$C_5$alkenyl, $C_2$–$C_5$haloalkenyl, $C_2$–$C_5$alkynyl, $C_3$–$C_7$cycloalkyl, phenyl, benzyl, furyl or tetrahydrofuryl.

Among this last mentioned group of compounds, particularly preferred compounds of the formula I are those in which $R_1$ is methyl, $R_2$ and $R_3$ are hydrogen and $R_4$ is hydrogen or the —$COR_5$ group, wherein $R_5$ is $C_1$–$C_3$alkyl, $C_1$–$C_3$alkoxy, $C_2$–$C_5$alkenyl, $C_2$–$C_5$haloalkenyl, $C_3$–$C_7$cycloalkyl, phenyl, benzyl, furyl or tetrahydrofuryl.

Particularly preferred compounds of the formula I are those in which $R_1$ is methyl, $R_2$ and $R_3$, each independently of the other, are hydrogen, methyl, ethyl, methoxy, bromine, cyano, nitro or amino, or both together in the ortho-position to each other as —(CH=CH)$_2$- group complete a naphthalene ring, and $R_4$ is hydrogen or, preferably, a hydrazinium ion, especially an ammonium ion.

Typical representatives of the compounds of formula I are e.g.:

4-hydroxy-3-nitrophenylmethylsulfone,
4-[3-chloro-n-propylcarbonyloxy]-3-nitrophenylmethylsulfone,
4-hydroxy-3-nitrophenylmethylsulfone tetra(n-butyl)ammonium salt,
4-acetyloxy-3-nitrophenylmethylsulfone,
4-cyclopropylcarbonyl-3-nitrophenylmethylsulfone,
4-hydroxy-3-nitrophenylethylsulfone,
4-acryloxy-3-nitrophenylmethylsulfone,
4-trichloroacryloxy-3-nitrophenylmethylsulfone,
4-n-propylcarbonyloxy-3-nitrophenylmethylsulfone,
4-ethylcarbonyloxy-3-nitrophenylmethylsulfone,
4-phenylcarbonyloxy-3-nitrophenylmethylsulfone,
4-methoxymethylcarbonyloxy-3-nitrophenylmethylsulfone,
4-cyclohexylcarbonyloxy-3-nitrophenylmethylsulfone,
4-chloromethylcarbonyloxy-3-nitrophenylmethylsulfone and
4-methoxycarbonyloxy-3-nitrophenylmethylsulfone.

Compounds of the formula I are obtained by hydrolising an aryl halide of the formula II

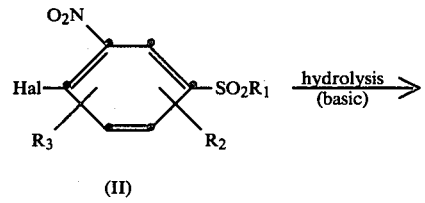

(II)

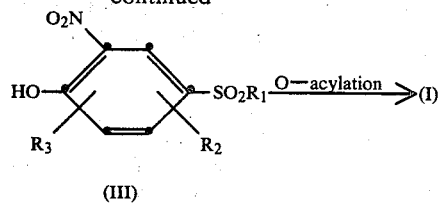

(III)

in the presence of a base, to an aromatic alcohol of the formula III and, if desired, acylating the compound of the formula III with a reactive derivative, preferably the anhydride or acid halide, most preferably, the acid chloride or acid bromide of the acid of the formula IV [$R_5$COOH (IV)], at the phenolic OH group, in a manner known per se, to an O-substituted product of the formula I, or by converting the compound of the formula III into a salt of the formula I by neutralisation of the OH group with a base, and isolating the resultant product in conventional manner. In the formulae II, III and IV above, the substituents $R_1$ to $R_5$ are as defined for formula I.

Hal is halogen. Examples of suitable bases are aqueous hydrazinium and ammonium hydroxide derivatives.

Inert solvents or diluents may be used in the acylation reaction. Examples of suitable solvents and diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxane, tetrahydrofurane; nitriles such as acetonitrile, propionitrile; N,N-dialkylated amides such as dimethyl formamide; dimethyl sulfoxide; ketones such as acetone, diethyl ketone, methyl ethyl ketone; and mixtures of such solvents with each other. In some cases the acylating agent itself may be used as solvent.

The presence of a reaction catalyst, such as dimethyl formamide, can be advantageous in the O-acylation reactions.

The reaction temperatures are generally in the range from 0° to 180° C., preferably from 0° to 150° C., or are at the boiling point of the solvent or mixture of solvents. In some cases it is advantageous to use acid acceptors or condensing agents, as examples of which there may be cited: tertiary amines such as trialkylamines (trimethylamine, triethylamine, tripropylamine etc.), pyridine and pyridine bases (4-dimethylaminopyridine, 4-pyrrolidinylaminopyridine etc.), oxides and hydroxides, carbonates and bicarbonates of alkali metals and alkaline earth metals, as well as alkali acetates.

Hydrogen halide formed during the reaction may also in some cases be expelled from the reaction mixture by introducing an inert gas, e.g. nitrogen, or removed from the mixture by the addition of a molecular sieve.

Whenever the described process results in hydrazinium or ammonium salts of the formula I, the preparatory method and the process product constitute objects of the present invention.

Biologically active nitroarylalkylsulfone derivatives are already known. For example, the compounds of formula I belong to a group of nitroarylalkylsulfones which are disclosed in British patent specification 1 128 217 as herbicides for controlling harmful plants. 5-Bromo-4-hydroxy-3-nitrophenylmethylsulfone and 5- iodo-4-hydroxy-3-nitrophenylmethylsulfone are specifically mentioned in this patent specification, whereas the other compounds of the formula I are embraced only in the most general form. The preparation and the chemical and physical properties of 4-hydroxy-3-nitrophenylmethylsulfone are described in Chem. Abstr. 53, 3110d (1959), and of 4-acetyloxy-3-nitrophenylmethylsulfone in Zhur. Obsh. Khim. 30, 3064–3072 (1960).

Surprisingly, it has now been found that nitroarylalkylsulfone derivatives of the formula I and compositions which contain these compounds have in particular the property that they influence the physiology of plants selectively. This influence on the physiological processes of plant development makes it possible to use the compounds of formula I for different purposes, e.g. those in connection with increasing the yield of useful plants and, in particular, with labour-saving in breeding and producing hybrid seeds.

Experience made so far with the application of growth regulators has shown that the compounds are able to influence the plants so as to bring about one or more different responses. These responses are largely dependent on the time of application, i.e. on the physiological state of the seed or on the development stage of the plant, on the nature of the application as well as, in particular, on the concentration employed. Such responses differ in turn, depending on the species of plant. The application of compounds of the formula I affords the possibility of influencing plant growth in the desired manner.

It is possible to regulate the growth of numerous monocot and dicot plants with the nitroarylalkylsulfone derivatives of the formula I and the agrochemical compositions which contain them, such that the vegetative growth is influenced advantageously in wide ranges of concentration for the crops concerned. Phytotoxic effects may occur when high rates of concentration are employed. The influence on the generative plant growth differs, depending on the crop plant.

An important way of regulating generative growth resides in the particular property of the nitroarylalkylsulfone derivatives of this invention to effect a gametocidal action in different cultivated plants, especially when these compounds are applied to monocot plants such as wheat, rye, barley, oats, rice, maize, sorghum, forage grasses etc., and also in other plants such as sunflowers or cotton. This action induces male sterility in the plants without noticeably influencing the fertility of the female flower parts. An increase in the flower shoots and/or the formation of parthenocarpic fruit (e.g. in tomatoes) is simultaneously observed in numerous cultivated plants. Male sterility is evidenced either in actual male sterility, viz. that the male flower parts are not formed at all or the pollen is sterile, or in a functional sterility in which the male flower parts are formed but are unable to cause pollination. The compounds of formula I are therefore also able to cause protogyny. i.e. female flower parts able to cause pollination are formed prematurely or the growth of male inflorescences is so delayed that cross-pollination with selected pollen can be carried out.

These gametocidal effects can be utilised with particular advantage in breeding and producing hybrid seeds. Hybrid seeds are of importance for growing the principal food plants and ornamentals. Hybrids are usually healthier than pure varieties and produce higher yields than the most productive parent variety.

To obtain hybrid seed, the breeder crosses two or more carefully selected inbreed lines in a procedure which has been worked out experimentally, and obtains in this manner hybrid seeds from which plants of increased growth and yield are grown.

Hybridisation of monoecious maize plants can also be effected in conventional manner, as male and female flower parts are formed at different parts of the plant (dioecious flowers). The anthers which yield pollen form the spike of the maize plant, whereas the spadiceous female inflorescence is formed with the stigmatic lobes below the centre of the plant. To breed $F_1$ hybrids, it is usual to plant alternating rows of maize plants of the AA and BB varieties or homozygotic lines. In order to ensure that the AA maize does not form any pollen, the AA plants are sterilised manually or mechanically before the male inflorescences fully develop and are then pollinated with pollen of a BB maize variety to form seeds of an AB hybrid ($F_1$) on the AA plants. The required procedure is not only time-consuming and complicated, but results inevitably in damage to the plant and —especially when sterilisation is effected mechanically—in an unwanted diminution in yield of the line/variety acting as female parent (seed plant).

Hybridisation of monoecious plants such as maize can still be carried out in a more or less economical manner by the above described conventional method. However, this procedure is much more difficult to employ for hybridising small grain cereals, especially those having hermaphroditic flowers and which are normally self-pollinating or also cross-pollinating. With these plants the conventional procedure is extremely time-consuming, labour-intensive and uneconomic and, in particular, requires specially trained personnel. It is only possible to breed small grain hybrids if the self-pollination and cross-pollination is completely inhibited in the parent plant. In practice this has to be done by opening each of the tiny flowers prematurely by hand, carefully removing all the anthers, and then protecting the flowers from unwanted cross-pollination.

Yet a further method of hybridisation is employed for some types of cereals, such as wheat, barley, sorghum, as well as maize and dicots. Cytoplasmic, male-sterile plants are used in this method and cross-pollination is effected.

These cytoplasmic sterile plants are limited to plant lines which have the same cytoplasma. As a consequence, cytoplasmically inherited weaknesses or defects, e.g. lack of resistance to a specific pathogen or susceptibility to frost and the like, are transferred by this method inevitably to all hybrids originating from this parent line. Moreover, hybridisation using cytoplasmically male-sterile lines, especially in the case of small grain cereals and also crops of dicots, requires complicated steps of more than ordinary difficulty.

Regardless of the method, it is essential for breeding hybrid seeds always to produce male-sterile and female-fertile plants. The use of chemical sterilisation agents (gametocides.) affords a simple, practicable and economic solution to the problem of inducing selective male sterility. Nitroarylalkylsulfone derivatives of the formula I have very good male-gametocidal properties and are therefore suitable for these and related purposes. When they are used in crops of useful plants, most of the problems which are associated with conventional methods of hybridisation do not arise at all.

In detail, the following procedure may be employed to produce male-sterile plants and thus to obtain hybrid seeds: The two parent plants to be crossed are planted e.g. in alternate rows. The line chosen as seed plant or parent plant is treated, at the start of flower formation, but before the formation of the male flower parts, with a compound of the formula I, to give a row of male-sterile but female-fertile parent plants. The other row is untreated and acts as pollen donor. Its male flower parts form fully and yield the pollen for pollinating the mother or seed plant. The seeds produced by the mother plant are the hybrids and can be harvested in conventional manner. The seeds of the male parent plants are harvested separately and used for other purposes.

The above described method of producing male-sterile plants and of obtaining hybrid seeds constitutes an object of the present invention.

In addition, the compounds of the formula I induce yet further growth regulating responses, for example a regulation of flower formation at the desired time and, as a consequence thereof, a controlled ripening of seeds and fruit. This kind of flower stimulation is of economic interest for those varieties of plant that simultaneously flower and bear fruit. For example, the treatment of avocado or cotton plants with compounds of the formula I may result, on the one hand, in an advantageous increase in the number of inflorescences and, on the other, the flowering and ripening process may be made subject to a controlled rhythm. Not only would it be possible to achieve in this manner an increase in yield, but also a more rational harvesting and thus better marketing of products.

This kind of stimulation of flower formation is also of importance in fruit growing. In general, as a consequence of genetic or external factors, an annual alternation between yield and non-yield years occurs in fruit growing. This alternation is the result of an imbalance between the growth of shoots and flowering, because the nourishment of the fruit cluster requires too many assimilation products at the expense of the formation of flower buds. The conventional measures for improving fruit quality consist in a time-consuming mechanical thinning of very young fruits as well as in a growth regulatory cutting of so-called wild shoots. This necessarily results in damage to the trees and in low yields. The use of nitroarylalkylsulfone derivatives of the formula I inhibits the growth of shoots substantially in favour of generative growth, so that growth contributes increasingly to flower and fruit formation. In this manner it is possible to improve not only the quality of the fruit, but also the yield, and to bring about a phase displacement in the alternation of yield and non-yield years.

In some cases the application of compounds of the formula I induces a marked prolongation of the flowering period, thereby increasing the possibility of pollinating all blossoms. An extension in time of the flowering phase is also desirable for numerous ornamental plants, especially flowers.

After numerous different cultivated plants have been treated with compounds of the formula I, a positive influence on the female inflorescences is observed parallel to the male sterilisation. In this manner the number of female flowers per inflorescence or per plant is increased, as is also the yield. Such responses are also observed in small grain cereals (such as barley), cucumber plants, sunflowers, legumes (such as soya beans), arborescent plants and ornamentals (composites). In some cases, further related growth regulating effects occur. In addition, a reduced susceptibility to frost and an increased resistance to pathogens in certain varieties of fruit can be observed.

Accordingly, the present invention also relates to the use of nitroarylalkylsulfone derivatives of the formula I, or of compositions which contain these compounds, for regulating plant growth, in particular for inducing sterility in male flower parts (utility as gametocides) and/or for promoting female flower parts and all secondary effects resulting therefrom, e.g. increase in yield, prolongation of the flowering phase, increased flower formation, regulation of fruiting or of the ripening process and the like.

In addition, the invention relates to the preparation of agrochemical compositions, comprising intimately mixing the active ingredient of the formula I with one or more substances or groups of substances described herein. The invention further relates to a method of treating plants, which comprises applying thereto compounds of the formula I or novel compositions containing them. The invention also relates to all novel compounds falling within the scope of the formula I, e.g. the salts, including the process for their production described herein.

Furthermore, it has been found that compounds of the formula I have for practical purposes a very useful microbicidal spectrum against phytopathogenic fungi and bacteria. They have very valuable curative, preventive, and systemic properties and can be used for protecting cultivated plants. With the compounds of the formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms. The compounds are effective in particular against fungus diseases such as rust, scab, powdery mildew and against fungi imperfecti (e.g. Puccinia, Rhizoctonia, Venturia, Erysiphe, Cercospora) as well as against bacteria of the family of the Pseudomonadaceae, especially Xanthomonas species. They can also be used as seed dressing agents for protecting seeds (fruit, tubers, grains) and plant cuttings against fungus infections as well as against phytopathogenic microorganisms which occur in the soil.

Accordingly, the invention also relates to microbicidal compositions and to the use of compounds of the formula I for controlling phytopathogenic microorganisms, especially harmful fungi and bacteria, and for the preventive treatment of plants to protect them from attack by such microorganisms.

Target crops to be protected within the scope of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetable (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

Nitroarylalkylsulfone derivatives may be applied preemergence or postemergence. However, postemergence application is preferred.

The rates of application depend on the desired growth regulating or microbicidal effect and should desirably be determined experimentally in accordance with the development stage and genus of plant, i.e. in accordance with the time of application. The following rules of thumb apply to the different fields of use. For growth regulation, especially for inducing a gametocidal response, the rates of application are in general in the range from 0.05 to 12, preferably from 0.5 to 8, most preferably from 1 to 4 kg of active ingredient per hectare (a.i./ha). A desirable time of application, especially for cereal crops, is the postemergence period, but still before the appearance of ears and anthers, i.e. the $5\frac{1}{2}$-leaf stage or the onset of flowering.

If it is desired to increase the number of inflorescences or to prolong the flowering phase, e.g. in sunflowers, cotton plants, cucumber plants (such as cucumbers, marrows and melons), legumes (such as beans, lentils, peas and soya beans) or ornamentals, then advantageous rates of application are in the range from 0.5 to 4 kg a.i./ha, whilst application is made necessarily before the start of flowering, in particular before the start of bud formation.

In plants such as cotton, in which flowering and fruit occur simultaneously, split application is desirable, i.e. application is preferably repeated periodically using lower rates of application. In general, the rates of application depend also on the type of application and, for simple leaf application, are preferably in the range from 2 to 6 kg a.i./ha, in split application from 2 to 4 kg a.i./ha and for soil (drench) application from 3 to 12 kg a.i./ha, depending on the type of soil.

For seed dressing the rates of application are in the range from about 0.02 to 1 kg a.i. per kg of seed. If the compounds of formula I are used as microbicides, advantageous rates of application are in the range from 0.5 to 5 kg/ha. In practice, however, the rates of application depend on the intensity of infestation of the microorganism to be controlled.

The above indicated rates of application and types of application likewise constitute an object of the invention.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying a compound of the formula I or an agrochemical composition which contains at least one of said compounds, is foliar (leaf) application. The number of applications and the rate of application depend on the intensity of infestation by the corresponding pathogen (type of fungus). However, the compounds of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating), by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosed in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepolite or bentonite; and suitable non-sorbent carriers are materials such as calcite or sand. In addition, a great number of preganulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl taurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$-alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)-ethylammonium bromide.

The surfactants customarily employed in the art of formulation are described e.g. in "McCutcheon's Detergents and Emulsifiers Annual", MC Publishing Corp. Ringwood, New Jersey, 1979, and Sisely and Wood, "Encyclopedia of Surface Active Agents", Chemical Publishing Co., Inc. New York, 1980.

The agrochemical composition usually contain 0.1 to 99%, preferably 0.1 to 95%, of a compound of the formula I, 1 to 99.9% of a solid or liquid adjuvant, and 0 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES (a) Preparation of

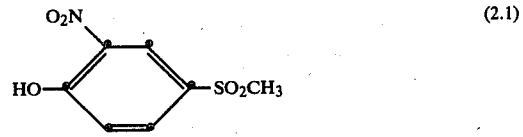
(2.1)

4-Hydroxy-3-nitrophenylmethylsulfone 25.6 kg of 4-chloro-3-nitrophenylmethylsulfone are stirred slowly into 4 kg of 30% aqueous sodium hydroxide and the mixture is diluted continuously with water to a volume of about 50 liters. The reaction mixture is heated to 90° C. and then a further 29 kg of 30% aqueous sodium hydroxide are added, with stirring, over 3 to 4 hours. The mixture is then heated for 90 minutes to 103° C. After it has cooled to about 60° C., the solution is adjusted with 16% sulfuric acid to a pH value of about 1.5, whereupon the product precipitates. The precipitate is isolated by filtration, washed and recrystallised from ethanol. Yield: 24 kg of colourless crystals with a melting point of 166°–168° C.

(b) Preparation of

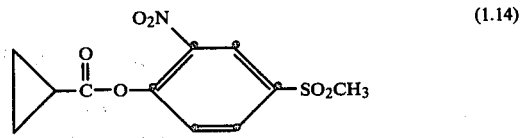
(1.14)

4-Cyclopropylcarbonyloxy-3-nitrophenylmethylsulfone 32.6 g of 4-hydroxy-3-nitrophenylmethylsulfone are suspended in 250 ml of tetrahydrofurane and to this suspension are added 21 ml of triethylamine. With stirring, 15.7 g of cyclopropanecarboxylic acid chloride are added dropwise to the resultant solution. After the weakly exothermic reaction has subsided, stirring is continued for 3 hours at room temperature and the filtrate is concentrated, affording 42 g of a viscous oil which is digested with petroleum ether. Yield: 40.5 g of pale yellow crystalline product with a melting point of 114°–116° C.

(c) Preparation of

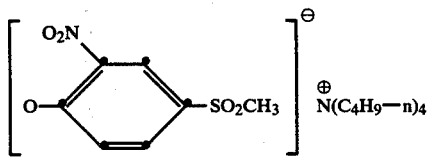 (2.20)

4-Hydroxy-3-nitrophenylmethylsulfone tetra-(n-butyl) ammonium salt

To a solution of 13.5 g of 4-hydroxy-3-nitrophenylmethylsulfone in 100 ml of ethanol are added 41 g of a 40% aqueous tetrabutylammonium hydroxide solution. The resultant deep yellow solution is evaporated in a rotovap to give 28 g of yellow crystal product with a melting point of 98°–100° C.

The compounds listed in Tables 1 and 2 can be prepared by procedures similar to those described in the foregoing Examples.

TABLE 1
Compounds of the formula V

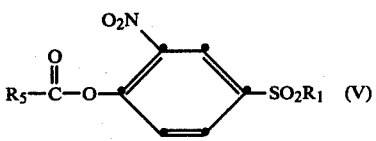 (V)

| Compound | $R_1$ | $R_5$ | Physical data (°C.) |
|---|---|---|---|
| 1.1 | $C_2H_5$ | $CCl=CCl_2$ | m.p. 89–91° |
| 1.2 | $CH_3$ | $CCl=CCl_2$ | m.p. 129–131° |
| 1.3 | $C_3H_7(n)$ | $CCl=CCl_2$ | resin |
| 1.4 | $C_3H_7(i)$ | $CCl=CCl_2$ | resin |
| 1.5 | $CH_3$ | $CH_3$ | m.p. 139–141° |
| 1.6 | $C_3H_7(n)$ | $CH_3$ | |
| 1.7 | $C_3H_7(i)$ | $CH_3$ | |
| 1.8 | $C_2H_5$ | $CH_3$ | m.p. 87–90,5° |
| 1.9 | $CH_3$ | $C_2H_5$ | m.p. 88–90° |
| 1.10 | $CH_3$ | $C_3H_7(n)$ | m.p. 83–85° |
| 1.11 | $CH_3$ | $C_3H_7(i)$ | m.p. 77–79° |
| 1.12 | $C_2H_5$ | $C_2H_5$ | m.p. 79–82° |
| 1.13 | $C_4H_9(n)$ | $CH_3$ | |
| 1.14 | $CH_3$ | cyclopropyl | m.p. 114–116° |
| 1.15 | $CH_3$ | cyclobutyl | |
| 1.16 | $CH_3$ | cyclopentyl | |
| 1.17 | $CH_3$ | cyclohexyl | m.p. 110–112° |
| 1.18 | $CH_3$ | cycloheptyl | |
| 1.19 | $CH_3$ | $C_4H_9(n)$ | m.p. 63–65° |
| 1.20 | $CH_3$ | $CH_2C(CH_3)_2CH_3$ | m.p. 89–91° |
| 1.21 | $C_2H_5$ | $C_4H_9(n)$ | |
| 1.22 | $C_2H_5$ | $CH_2C(CH_3)_2CH_3$ | |
| 1.23 | $CH_3$ | $(CH_2)_{10}CH_3$ | m.p. 84–87° |
| 1.24 | $CH_3$ | $CH=CH_2$ | m.p. 114–117° |
| 1.25 | $C_2H_5$ | $CH=CH_2$ | |
| 1.26 | $C_3H_7(n)$ | $CH=CH_2$ | |
| 1.27 | $C_2H_5$ | $CH=CHCH_3$ | m.p. 71–75° |

TABLE 1-continued
Compounds of the formula V

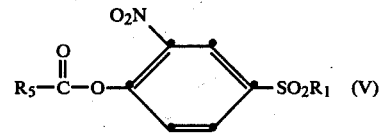 (V)

| Compound | $R_1$ | $R_5$ | Physical data (°C.) |
|---|---|---|---|
| 1.28 | $CH_3$ | $CH=CHCH_3$ | m.p. 100–102° |
| 1.29 | $C_2H_5$ | $CH=C(CH_3)_2$ | |
| 1.30 | $C_2H_5$ | $C(CH_3)=CHCH_3$ | |
| 1.31 | $CH_3$ | $CH=C(CH_3)_2$ | m.p. 88–90° |
| 1.32 | $CH_3$ | $C(CH_3)=CHCH_3$ | m.p. 87–89° |
| 1.33 | $CH_3$ | $CH_2Cl$ | m.p. 108–110° |
| 1.34 | $CH_3$ | $C_2H_4Cl$ | m.p. 123–125° |
| 1.35 | $C_2H_5$ | $CH_2Cl$ | m.p. 69–72° |
| 1.36 | $C_2H_5$ | $C_2H_4Cl$ | |
| 1.37 | $CH_3$ | $CHCl_2$ | |
| 1.38 | $CH_3$ | $CCl_3$ | |
| 1.39 | $CH_3$ | $(CH=CH)_2CH_3$ | m.p. 112–114° |
| 1.40 | $C_2H_5$ | $(CH=CH)_2CH_3$ | m.p. 88–93° |
| 1.41 | $CH_3$ | $(CH_2)_8CH=CH_2$ | m.p. 56–58° |
| 1.42 | $C_3H_7(i)$ | $CCl=CHCH_3$ | |
| 1.43 | $CH_3$ | $CCl=CHCH_3$ | m.p. 120–122° |
| 1.44 | $CH_3$ | $OCH_3$ | m.p. 163–165° |
| 1.45 | $C_2H_5$ | $OCH_3$ | |
| 1.46 | $C_3H_7(n)$ | $OCH_3$ | |
| 1.47 | $CH_3$ | $OC_2H_5$ | |
| 1.48 | $CH_3$ | $OC_3H_7(i)$ | |
| 1.49 | $CH_3$ | $CH_2Br$ | m.p. 98–100° |
| 1.50 | $CH_3$ | $CH_2I$ | |
| 1.51 | $CH_3$ | $CF_3$ | |
| 1.52 | $CH_3$ | $O(CH_2)_3Cl$ | m.p. 87–89° |
| 1.53 | $CH_3$ | $OC_2H_4Cl$ | |
| 1.54 | $CH_3$ | $OC_4H_2Br$ | |
| 1.55 | $CH_3$ | $CCl=CHCl$ | m.p. 129–130° |
| 1.56 | $C_2H_5$ | $CCl=CHCl$ | |
| 1.57 | $CH_3$ | $CH_2OC_2H_5$ | |
| 1.58 | $CH_3$ | $(CH_2)_2OCH_3$ | |
| 1.59 | $CH_3$ | $CH_2OCH_3$ | m.p. 91–92° |
| 1.60 | $C_2H_5$ | $CH_2OCH_3$ | |
| 1.61 | $C_2H_5$ | $C_6H_5$ | |
| 1.62 | $CH_3$ | $C_6H_5$ | m.p. 142–144° |
| 1.63 | $CH_3$ | $C_6H_4(4-Cl)$ | |
| 1.64 | $CH_3$ | $C_6H_4(3-Cl)$ | |
| 1.65 | $CH_3$ | $C_6H_4(2-Cl)$ | |
| 1.66 | $C_2H_5$ | $C_6H_4(4-Cl)$ | |
| 1.67 | $CH_3$ | $C_6H_4(4-NO_2)$ | m.p. 205–208° |
| 1.68 | $CH_3$ | $C_6H_3Cl_2(2,4)$ | |
| 1.69 | $CH_3$ | $C_6H_4(4-F)$ | m.p. 157–159° |
| 1.70 | $CH_3$ | $C_6H_4(4-CF_3)$ | |
| 1.71 | $C_2H_5$ | $C_6H_4(4-NO_2)$ | |
| 1.72 | $CH_3$ | $C_6H_3(NO_2)_2(2,4)$ | |
| 1.73 | $CH_3$ | $CH=CHC_6H_5$ | m.p. 152–155° |
| 1.74 | $C_2H_5$ | 2-tetrahydrofuryl | resin |
| 1.75 | $CH_3$ | 2-tetrahydrofuryl | resin |
| 1.76 | $C_2H_5$ | 2-furyl | |
| 1.77 | $CH_3$ | 2-furyl | m.p. 173–175° |
| 1.78 | $CH_3$ | $(CH_2)_3Cl$ | m.p. 83–85° |
| 1.79 | $CH_3$ | $CHBrCH_3$ | m.p. 89–92° |
| 1.80 | $CH_3$ | $C(CH_3)_3$ | 117–119° |

TABLE 2
Compounds of the formula I $$R_4O-\underset{R_3}{\overset{O_2N}{\bigcirc}}-SO_2R_1 \quad (I)$$

| Compound | $R_1$ | $R_2$ | $R_3$ | $R_4$ | Physical data (°C.) |
|---|---|---|---|---|---|
| 2.1 | $CH_3$ | H | H | H | m.p. 166–168° |

TABLE 2-continued

Compounds of the formula I

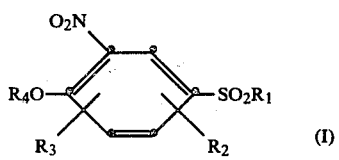

(I)

| Compound | R₁ | R₂ | R₃ | R₄ | Physical data (°C.) |
|---|---|---|---|---|---|
| 2.2 | C₂H₅ | H | H | H | m.p. 138° |
| 2.3 | CH₃ | 6-Br | H | H | |
| 2.4 | CH₃ | 6-J | H | H | |
| 2.5 | CH₃ | 6-CH₃ | H | H | |
| 2.6 | CH₃ | 6-Br | 5-Br | H | |
| 2.7 | CH₃ | 6-NO₂ | H | H | |
| 2.8 | CH₃ | 6-C₃H₇—i | H | H | |
| 2.9 | CH₃ | 6-CF₃ | H | H | |
| 2.10 | C₃H₇—n | H | H | H | |
| 2.11 | C₃H₇—i | H | H | H | |
| 2.12 | CH₃ | H | H | ½Cu⁺⁺ | |
| 2.13 | CH₃ | H | H | Na⁺ | |
| 2.14 | CH₃ | H | H | ⅓Al⁺⁺⁺ | |
| 2.15 | CH₃ | H | H | Mn⁺⁺ | |
| 2.16 | CH₃ | 6-CH₃ | 5-CH₃ | H | |
| 2.17 | CH₃ | 6-NH₂ | H | H | |
| 2.18 | CH₃ | 6-Cl | 5-Cl | H | |
| 2.19 | CH₃ | H | H | N(CH₃)₄⁺ | m.p. 151–153° |
| 2.20 | CH₃ | H | H | N(C₄H₉—n)₄⁺ | m.p. 98–100° |
| 2.21 | CH₃ | H | H | N(C₂H₅)₄⁺ | m.p. 130–137° |
| 2.22 | CH₃ | H | H | N(CH₃)₃CH₂C₆H₅⁺ | orange yellow resin |
| 2.23 | CH₃ | H | H | N(CH₃)₃C₁₂H₂₅⁺ | orange resin |
| 2.24 | CH₃ | H | H | N(CH₃)₂N(CH₃)₃⁺ | orange resin |
| 2.25 | CH₃ | H | H | NH₂NH₃⁺ | |

Formulation Examples for Liquid Active Ingredients of the Formula I (throughout, percentages are by weight)

| 1. Emulsifiable concentrates | (a) | (b) | (c) |
|---|---|---|---|
| Compound of Table 1 or 2 | 25% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexane | — | 15% | 20% |
| xylene mixture | 65% | 25% | 20% |

Emulsions of any required concentration can be produced from such concentrates by dilution with water.

| 2. Solutions | (a) | (b) | (c) | (d) |
|---|---|---|---|---|
| Compound of Table 1 or 2 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| Compound of Table 1 or 2 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
|---|---|---|
| Compound of Table 1 or 2 | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation Examples for Solid Active Ingredients of the Formula I (throughout, percentages are by weight)

| 5. Wettable powders | (a) | (b) | (c) |
|---|---|---|---|
| Compound of Table 1 or 2 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. | Emulsifiable concentrate | |
|---|---|---|
| | Compound of Table 1 or 2 | 10% |
| | octylphenol polyethylene glycol ether (4–5 moles of ethylene oxide) | 3% |
| | calcium dodecylbenzenesulfonate | 3% |
| | caster oil polyglycol ether (36 moles of ethylene oxide) | 4% |
| | cyclohexanone | 20% |
| | xylene mixture | 50% |
| | coconut oil | 10%. |

Emulsions of any required concentration can be obtained from this concentrate by dilution with water.

| 7. | Dusts | (a) | (b) | (c) |
|---|---|---|---|---|
| | Compound of Table 1 or 2 | 5% | 8% | 6% |
| | talcum | 95% | — | 44% |
| | Kaolin | — | 92% | 50% |

Ready for use dusts are obtained by mixing the active ingredient with the carriers, and grinding the mixture in a suitable mill.

| 8. | Extruder granulate | |
|---|---|---|
| | Compound of Table 1 or 2 | 10% |
| | sodium lignosulfonate | 2% |
| | carboxymethylcellulose | 1% |
| | kaolin | 87%. |

The active ingredient is mixed and ground with the adjuvants, and the mixture is subsequently moistened with water. The mixture is extruded and then dried in a stream of air.

| 9. | Coated granulate | (a) | (b) |
|---|---|---|---|
| | Compound of Table 1 or 2 | 3% | 5% |
| | polyethylene glycol 200 | 3% | 3% |
| | kaolin | 94% | 92% |

The finely ground active ingredient is uniformly applied, in a mixer, to the kaolin moistened with polyethylene glycol. Non-dusty coated granulates are obtained in this manner.

| 10. | Suspension concentrate | |
|---|---|---|
| | Compound of Table 1 or 2 | 40% |
| | ethylene glycol | 10% |
| | nonylphenol polyethylene glycol ether (15 moles of ethylene oxide) | 6% |
| | sodium lignosulfonate | 10% |
| | carboxymethylcellulose | 1% |
| | 37% aqueous formaldehyde solution | 0.2% |
| | silicone oil in the form of a 75% aqueous emulsion | 0.8% |
| | water | 32%. |

The finely ground active ingredient is intimately mixed with the adjuvants, giving a suspension concentrate from which suspensions of any desired concentration can be obtained by dilution with water. Formulation ingredients which enhance the adhesion of the active ingredient to the plant, e.g. mineral or vegetable oils, are very effective in foliar application.

BIOLOGICAL EXAMPLES

Example 11: Gametocidal activity in small grain cereals (a) Induction of male sterility Wheat plants are sprayed at the start of flower formation, i.e. in about the 5½-leaf stage, with a spray mixture (concentration 3000 ppm) prepared from an active ingredient formulated as wettable powder. Two to four weeks after application, but before the appearance of the anthers, each ear is covered to protect it against cross-pollination. Evaluation of the gametocidal activity is made at harvest time by counting the number of grains per ear. Untreated wheat plants are used for comparison purposes.

(b) Fertility test (formation of hybrid seeds)

A control group of wheat plants is treated as in (a), covered or kept isolated, and cross-pollinated with pollen of another variety of wheat. Evaluation of fertility is made at harvest time by counting the number of hybrid grains formed in each ear. Untreated wheat plants and treated, but covered, plants are used for comparison purposes.

In tests (a) and (b) above, nitroarylalkylsulfone derivatives of Tables 1 and 2 exhibit very good gametocidal activity in wheat. Compounds 1.1, 1.2, 1.5, 1.9, 1.10, 1.11, 1.14, 1.17, 1.19, 1.20, 1.23, 1.24, 1.28, 1.31, 1.32, 1.33, 1.34, 1.39, 1.41, 1.43, 1.44, 1.49, 1.52, 1.55, 1.59, 1.62, 1.67, 1.69, 1.73, 1.77–1.79, 2.1, 2.2 and 2.19–2.21 reduce the formation of grains in each ear to 0–15%. Even at a concentration of 750 ppm, compounds 1.2, 1.5, 1.14, 1.24, 2.1 and 2.20, among others, still inhibit the formation of grains completely (untreated control=100% grain formation).The second control group treated with the cited compounds (test b) develops in the same way as the untreated plants after cross-pollination. The yield of harvested hybrid grains is 85 to 100%. The number of hybrid grains in wheat plants treated with one of compounds 1.2, 1.5, 1.14, 1.24, 2.1 and 2.20 is even higher than in the untreated control group. Comparable results are obtained in similar tests with barley and rye.

Example 12: Gametocidal activity in maize (a) Induction of male sterility

Maize plants are sprayed uniformly during flower formation, but before the male inflorescence appears, with a suspension of the active ingredient (concentration 3000 ppm). Spike and tassel of the treated plants are carefully covered. After the male flower parts have formed, i.e. about 3 weeks after application, the gametocidal activity is evaluated from the formation of tassels and anthers and the pollen sterility is tested by effecting self-fertilisation. This is done by transferring, as soon as it has formed, pollen from the same plant to the stigma of the spikes (self-fertilisation) and counting the number of maize seeds in each spike at harvest time. Untreated maize is used for comparison purposes.

(b) Fertility test (formation of hybrid seeds)

A control group of maize plants is treated as in (a) and the male and female flower parts are carefully covered. About 3 weeks after application, the spikes of the treated plants are cross-pollinated with pollen of another selected maize variety. The fertility is evaluated at harvest time by counting the number of hybrid seeds in each spike. Untreated maize plants are used for comparison purposes.

In the above tests (a) and (b), compounds of Tables 1 and 2 induce almost complete male sterility. For example, treatment with compounds 1.1, 1.2, 1.5, 1.9, 1.14, 1.17, 1.19, 1.20, 1.24, 1.28, 1.31 to 1.35, 1.41, 1.43, 1.44, 1.49, 1.55, 1.59, 1.62, 1.69, 1.77, 1.78, 1.79, 2.1, 2.2 and 2.19 to 2.21, results in a reduction of maize seeds in each spike to less than 20%. At a concentration of 2000 ppm, compounds 1.2, 1.5, 1.14, 1.24, 1.77, 2.1, 2.2, 2.19 and 2.20 still inhibit seed formation completely (untreated controls=100% seed formation). None of the compounds impairs cross-pollination noticeably. The yield of hybrid seeds is 85 to 100%.

Example 13: I—Gametocidal activity in sunflowers (foliar application)

(a) Induction of male sterility

Sunflower plants of a self-fertilising variety are sprayed uniformly with an emulsion of the active ingredient (concentration 3000 ppm) about 3 weeks before the start of flowering. The inflorescence buds of the treated plants are carefully covered to protect them from cross-pollination and, at harvest time, the gametocidal activity is evaluated by counting the number of full seeds still formed. Untreated sunflowers are used for comparison purposes.

(b) Fertility test (formation of hybrid seeds)

A control group of sunflower plants is treated as in (a). The buds of the treated plants are carefully covered. After the flowers have opened, cross-pollination is effected with pollen of another selected sunflower variety. This is done by introducing the fertile pollen into the covering. Evaluation of fertility is made at harvest time by counting the number of hybrid seeds. Untreated sunflowers are used for comparison purposes.

II—Gametocidal activity in sunflowers (soil application)

(a) Induction of male sterility

Sunflowers of a self-fertilising variety are planted in pots. 3–6 weeks before the start of flowering, the soil in the pots is watered with a spray mixture obtained from the active ingredient formulated as wettable powder (concentration 0.006%), based on the volume of the soil. Care is taken that the parts of the plant above the soil remain unwetted. The buds of the treated plants are carefully covered and, at harvest time, the gametocidal activity is evaluated by counting the number of full seeds still formed as compared with untreated sunflowers.

(b) Fertility test (formation of hybrid seeds)

A control group of sunflower plants is planted in pots and treated as in (a). The buds of the treated plants are carefully covered. After the flowers have opened, cross-pollination is effected with pollen of another selected sunflower variety. This is done by introducing the pollen into the covering. Evaluation is made at harvest time by counting the number of hybrid seeds formed. Untreated sunflowers are used for comparison purposes.

In the above tests I and II, the compounds of Tables 1 and 2 exhibit a comparable gametocidal activity. Treatment with one of compounds 1.1, 1.2, 1.5, 1.9, 1.10, 1.11, 1.14, 1.17, 1.19, 1.24, 1.28, 1.31, 1.32, 1.33, 1.34, 1.35, 1.39, 1.41, 1.43, 1.44, 1.49, 1.52, 1.55, 1.59, 1.62, 1.67, 1.69, 1.73, 1.77–1.79, 2.1, 2.2 and 2.19–2.24 inhibits the formation of seeds to less than 15% as compared with untreated plants. Compounds 1.1, 1.2, 1.5, 1.14, 1.24, 1.77, 2.1, 2.2 and 2.19 to 2.24 even induce 100% male sterility, but cross-pollination is not noticeably influenced and results in a yield of hybrid seeds of 80 to 100%.

Example 14: Flower stimulation in cotton

Before the start of flowering, cotton plants are sprayed uniformly with an aqueous dispersion of active ingredient (concentration 500 ppm) and application is repeated at intervals of 1 to 3 weeks, depending on the growth rate. Capsule and seed formation are evaluated at harvest time as compared with untreated control plants. Compounds of Tables 1 and 2 induce in cotton plants a marked stimulatory response to flower formation. Repeated treatment with one of compounds 1.1, 1.2, 1.5, 1.9, 1.10, 1.11, 1.14, 1.17, 1.19, 1.28, 1.31, 1.32, 1.33, 1.34, 1.35, 1.39, 1.41, 1.43, 1.44, 1.49, 1.52, 1.55, 1.59, 1.62, 1.67, 1.69, 1.73, 1.77–1.79, 2.1, 2.2 and 2.19–2.21 increases the number of inflorescences by 5 to 25% compared with control plants. The plants have a healthy appearance and have a qualitatively normal capsule and seed formation.

Example 15: Gametocidal activity in tomatoes (a) Induction of male sterility Before the start of flowering, tomato plants are uniformly sprayed with a spray mixture prepared from a wettable powder formulation of the active ingredient (concentration 1000 ppm), the application being repeated at intervals in accordance with the growth rate of the plants. Evaluation of the gametocidal activity is made at harvest time by counting the number of seeds in the completely formed fruit of each plant. Untreated tomato plants are used for comparison purposes.

(b) Fertility test

A group of control plants is treated as in (a), except that cross-pollination is effected during flowering with selected pollen of another tomato variety. The fertility of the treated plants is evaluated at harvest time by counting the number of seeds in the completely formed fruit of each plant, using untreated tomato plants for comparison purposes.

In the above test, compounds of Tables 1 and 2 exhibit very good gametocidal properties in tomato crops. Treatment with one of compounds 1.1, 1.2, 1.5, 1.9, 1.10, 1.11, 1.14, 1.17, 1.19, 1.24, 1.28, 1.31, 1.32, 1.33, 1.34, 1.35, 1.39, 1.41, 1.43, 1.44, 1.49, 1.52, 1.55, 1.59, 1.62, 1.67, 1.69, 1.73, 1.77–1.79, 2.1, 2.2, 2.19, 2.20, 2.21 and 2.22 reduces the size of the fruit compared with untreated plants, and at the same time it is observed that the fruit contains fewer or no seeds. Treatment with one of compounds 1.1, 1.2, 1.5, 1.14, 1.24, 1.77 and 2.1 induces complete male sterility, and cross-pollination is not noticeably influenced. The same also applies to compounds 2.19 and 2.20.

Example 16: Gametocidal activity in leguminous plants (a) Induction of male sterility (postemergence treatment)

Dwarf beans of the "Miry" variety are uniformly sprayed in the bud stage of flowering with a suspension of the active ingredient (concentration 2000 ppm) and the buds are then carfully covered. After flowering has occurred, the pollen formation is evaluated and the sterility of the pollen is tested by cross-pollination with selected flowers of untreated control plants which have been sterilised by hand. Similar cross-pollination of untreated plants is performed for control purposes. In a parallel test, a drench application (soaking the root zone with 4 kg/a.i./ha) is substituted for the foliar application.

(b) Fertility test

A control group of dwarf beans is treated as in (a) and the buds are carefully covered. After the flowers have opened, they are pollinated with pollen of untreated flowers and the fertility rate is compared with that of cross-pollinated, untreated flowers of test (a) which have been sterilised by hand.

In the above tests, compounds 1.1, 1.2, 1.5, 1.9, 1.10, 1.11, 1.14, 1.17, 1.19, 1.20, 1.23, 1.24, 1.27, 1.28, 1.31–1.34, 1.39, 1.40, 1.41, 1.43, 1.44, 1.49, 1.52, 1.55, 1.59, 1.67, 1.69, 1.73, 1.77–1.79, 2.1, 2.20 and 2.21 induce a pollen reduction of 85 to 90% and a pollen sterility of 90 to 100% compared with untreated control plants whose pollen is fully formed and fertile. When cross-pollinating with pollen of untreated plants, no noticeable influence on the female flower parts is observed (95–100% fruit formation), but some parthenocarpic fruit is formed.

Example 17: Gametocidal activity in flax (a) Induction of male sterility

Flax of the "Blaublühender" variety is uniformly sprayed in the bud stage with a suspension of the active ingredient (concentration 500 and 100 ppm) and the buds are then carefully covered. After the flowers have formed, the pollen formation is evaluated and pollen sterility is treated by cross-fertilisation with selected flowers of untreated control plants which have been sterilised by hand. Similar cross-fertilisation of untreated plants is effected for comparison purposes. In a parallel test, a drench application (soaking the root zone with 3 kg/a.i./ha) is substituted for the foliar application.

(b) Fertility test

A control group of flax plants is treated as in (a) and the buds are carefully covered. After the flowers have opened, they are pollinated with pollen of untreated plants and the fertility rate is compared with that of cross-pollinated, untreated flowers of test (a) which have been sterilised by hand.

In the above tests, compounds 1.1, 1.2, 1.5, 1.9, 1.10, 1.11, 1.17, 1.20, 1.23, 1.24, 1,27, 1.28, 1.31–1.34, 1.39, 1.40, 1.41, 1.43, 1.44, 1.49, 1.52, 1.55, 1.59, 1.67, 1.69, 1.73, 1.77–1.79, 2.1, 2.2 and 2.19–2.21 induce a pollen reduction of about 90% and almost complete male sterility (95 to 100%) of the pollen compared with untreated control plants, the pollen of which is fully formed and fertile. When cross-pollinating with pollen of untreated plants, no noticeable influence on the female flower parts of treated plants is observed (95–100% fruit formation), but some parthenocarpic fruit is formed.

Example 18: Action against *Cercospora arachidicola* in groundnut plants (a) Residual-protective action Groundnut plants 10–15 cm in height are sprayed with a spray mixture prepared from a wettable powder formulation of the active ingredient (concentration 0.02%) and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection, and is based on the number and size of the specks.

(b) Systemic action

Groundnut plants 10–15 cm in height are sprayed with a spray mixture prepared from a wettable powder formulation of the active ingredient (0.006%, based on the volume of the soil). The treated plants are infected 48 hours later with a conidia suspension of the fungus and then incubated for 72 hours at about 21° C. and high humidity. The plants are then stood in a greenhouse and evaluation of fungus attack is made 11 days later. Compared with untreated and infected controls (number and size of the specks=100%), the plants treated with compounds of Tables 1 and 2 exhibit greatly reduced attack by Cercospora.

In the above tests, compounds 1.1, 1.2, 1.24, 1.31, 1.35, 1.43, 1.79, 1.80, 2.1 and 2.2 prevent speck development almost completely (0 to 10%).

Example 19: Action against *Puccinia graminia* on wheat (a) Residual-protective action Wheat plants are treated 6 days after sowing with a spray mixture prepared from a wettable powder formulation of the active ingredient (0.06%). After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture prepared from a wettable powder formulation of the active ingredient (0.06% based on the volume of the soil). After 48 hours the treated plants are infected with a uredospore suspension of the fungus. The plants are then incubated for 48 hours at 95–100% relative humidity and about 20° C. and then stood in a greenhouse at about 22° C. Evaluation of rust pustule development is made 12 days after infection. Compounds of formula I are very effective against Puccinia fungi. 100% Puccinia attack is found on untreated and infected control plants. Among others, compounds 1.33, 1.34, 1.35, 1.78, 1.79 and 1.80 inhibit fungus attack to 0–5%.

Example 20: Action against *Erysiphe graminis* on barley (a) Residual protective action Barley plants about 8 cm in height are sprayed with a spray mixture (0.02%) prepared from the active ingredient formulated as a wettable powder. The treated plants are dusted with conidia of the fungus after 3–4 hours. The infected barley plants are then stood in a greenhouse at about 22° C. The fungus attack is evaluated after 10 days.

(b) Systemic action

Barley plants about 8 cm in height are treated with a spray mixture (0.006%, based on the volume of the soil) preprared from the active ingredient formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and evaluation of infestation is made after 10 days.

Compounds of the formula I are very effective against Erysiphe fungi. 100% Erysiphe attack is found on untreated and infected control plants. Among others, compounds 1.1, 1.2, 1.24, 1.33, 1.34, 1.78, 1.79 and 1.80 inhibit fungus attack to less than 10%.

Example 21: Action against *Xanthomonas oryzae* in rice (a) Residual-protective action Three weeks after being reared in a greenhouse, rice plants of the variety "Caloro" or "S6" are sprayed with the compound for testing in the form of a wettable powder (0.06% concentration). The spray coating is left to dry for 1 day and the plants are then put into a climatic chamber at 24° C. and 75-85% relative humidity and infected by cutting off the tips of the leaves with scissors which have been dipped beforehand in a suspension of *Xanthomonas oryzae*. After incubation for 10 days in the same room, the cut leaves wither, roll up and become necrotic. The residual action of the test compound is assessed by determining the extent of these symptoms.

(b) Systemic action

Three weeks after being reared in a greenhouse, rice plants of the variety "Caloro" or "S6" are sprayed with the compound for testing in the form of a wettable powder (0.006% concentration). Three days after this treatment the plants are put into a climatic chamber at 24° C. and 75-85% relative humidity and infected by cutting off the tips of the leaves with scissors which have been dipped beforehand in a suspension of *Xenthomonas oryzae*. After incubation for 10 days in the same room, the cut leaves wither, roll up and become necrotic. The residual action of the test compound is assessed by determining the extent of these symptoms. Compounds of Tables 1 and 2 are very effective against Xanthomonas bacteria and, in the residual-protective treatment of rice, compounds 1.1, 1.2, 1.5, 1.9, 1.10, 1.11, 1.14, 1.19, 1.20, 1.23, 1.24, 1.28, 1.31, 1.32, 1.34, 1.35, 1.39, 1.41, 1.43, 1.44, 1.49, 1.52, 1.59, 1.69, 1.73, 1.77, 2.1 and 2.2, among others, inhibit the occurrence of necrotic specks almost completely (0 to 5%). In addition, compounds 1.1, 1.2, 1.5, 1.9, 1.10, 1.11, 1.19, 1.20, 1.23, 1.24, 1.28, 1.31, 1.32, 1.34, 1.39 1.41, 1.43, 1.49, 1.52, 1.59, 1.69, 1.73, 2.1 and 2.2 also have a fully effective systemic action (0 to 5% necrosis). 100% necrosis is found in untreated but infected rice plants (controls).

Example 22: Action against *Xanthomonas vesicatoria* in paprika (a) Residual-protective action Three weeks after they have been reared in a greenhouse, paprika plants of the "California Wonder" variety are sprayed with the compound to be tested in the form of a spray mixture (concentration 0.06%). This spray coating is allowed to dry for 1 day and then the plants are stood in a climatic chamber at 26° C. and 95-100% relative humidity and infected by spraying the underside of the leaves with a standardised suspension of *Xanthomonas vesicatoria*. After incubation for 6 days in the same room, round, initially watery, then later necrotic, specks appear on the leaves. The residual action of the test compound is evaluated by determining the extent of these specks.

(b) Systemic action

Three weeks after they have been reared in a greenhouse, paprika plants of the "California Wonder" variety are wetted with a suspension of the test compound (0.006%, based on the volume of the soil). Three days after this treatment, the plants are stood in a climatic chamber at 26° C. and 95-100% relative humidity and infected by spraying the underside of the leaves with a standardised suspension of *Xanthomonas vesicatoria*. After incubation for 6 days in the same room, round, initially watery, then later necrotic, specks appear on the leaves. The residual action of the test compound is evaluated by determining the extent of these specks. Compounds of both tables inhibit the occurrence of specks almost completely.

What is claimed is:

1. A method of stimulating flower formation in plants, which comprises treating said plants, parts of plants, seeds thereof or the locus thereof, with a compound of the formula

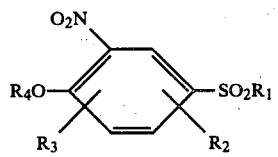

wherein
$R_1$ is $C_1-C_6$ alkyl,
each of $R_2$ and $R_3$ is hydrogen, $C_1-C_6$ alkyl, $C_1-C_6$ alkoxy, $C_1-C_6$ haloalkyl, halogen, cyano, nitro or amino, and
$R_4$ is hydrogen, an ammonium cation of the formula

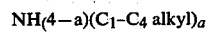

in which a is 1, 2, 3 or 4, or $R_4$ represents the —$COR_5$ group in which $R_5$ is $C_1-C_{12}$ alkyl, $C_1-C_{12}$ alkoxy, $C_1-C_{12}$ haloalkoxy, $C_2-C_{10}$ alkenyl, $C_2-C_{10}$ haloalkenyl, $C_3-C_7$ cycloalkyl, phenyl, furyl or phenyl substituted by halogen, nitro or vinyl.

2. A method according to claim 1 in which, in the compound,
$R_1$ is $C_1-C_3$ alkyl,
each of $R_2$ and $R_3$ is hydrogen, $C_1-C_3$ alkyl, $C_1-C_3$ alkoxy, $C_1-C_3$ haloalkyl, halogen, cyano, nitro or amino, and
$R_4$ is hydrogen, or the —$COR_5$ group in which $R_5$ is $C_1-C_6$ alkyl, $C_1-C_6$ alkoxy, $C_1-C_6$ haloalkoxy, $C_1-C_5$ alkenyl, $C_2-C_5$ haloalkenyl, $C_3-C_7$ cycloalkyl, phenyl, furyl or phenyl substituted by fluorine, nitro or vinyl.

3. A method according to claim 1 in which the compound is an ammonium salt whose cation has the formula

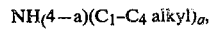

in which a is 1, 2, 3 or 4.

4. A method according to claim 2 in which
$R_1$ is methyl or ethyl,
$R_2$ is hydrogen, $R_3$ is hydrogen, methyl, methoxy, trifluoromethyl, bromine, cyano, nitro or amino, and $R_4$ is hydrogen, or the —$COR_5$ group in which $R_5$ is $C_1$–$C_3$ alkyl, $C_1$–$C_3$ alkoxy, $C_1$–$C_3$ haloalkoxy, $C_2$–$C_5$ alkenyl, $C_2$–$C_5$ haloalkenyl, $C_3$–$C_7$ cycloalkyl, phenyl, or furyl.

5. A method according to claim 4 in which
$R_1$ is methyl,
$R_3$ is hydrogen, and
$R_4$ is hydrogen, or the —$COR_5$ group in which $R_5$ is $C_1$–$C_3$ alkyl, $C_1$–$C_3$ alkoxy, $C_2$–$C_5$ alkenyl, $C_2$–$C_5$ haloalkenyl, $C_3$–$C_7$ cycloalkyl, phenyl, or furyl.

6. A method according to claim 2 in which the compound is selected from the group consisting of
4-hydroxy-3-nitrophenylmethylsulfone,
4-[3-chloro-n-propylcarbonyloxy]-3-nitrophenylmethylsulfone,
4-hydroxy-3-nitrophenylmethylsulfone-tetra(n-butyl)ammonium salt,
4-acetyloxy-3-nitrophenylmethylsulfone,
4-cyclopropylcarbonyl-3-nitrophenylmethylsulfone,
4-hydroxy-3-nitrophenylethylsulfone,
4-acryloxy-3-nitrophenylmethylsulfone,
4-trichloroacryloxy-3-nitrophenylmethylsulfone,
4-n-propylcarbonyloxy-3-nitrophenylmethylsulfone,
4-ethylcarbonyloxy-3-nitrophenylmethylsulfone,
4-phenylcarbonyloxy-3-nitrophenylmethylsulfone,
4-methoxymethylcarbonyloxy-3-nitrophenylmethylsulfone,
4-cyclohexylcarbonyloxy-3-nitrophenylmethylsulfone,
4-chloromethylcarbonyloxy-3-nitrophenylmethylsulfone and
4-methoxycarbonyloxy-3-nitrophenylmethylsulfone.

7. The method according to claim 6 in which the compound is 4-hydroxy-3-nitrophenylmethylsulfone.

8. A method according to claim 1, which comprises treating cultivated plants.

9. A method according to claim 8, which comprises treating small grain plants, cereals or forage grasses.

10. A method according to claim 8, which comprises treating wheat, rye, barley, oats, rice, maize, sorghum, flax, avocados, leguminosae, sunflowers, cotton, vegetables or ornamentals.

11. A method according to claims 1, 2, 3, 4, 5, 6 or 7 wherein the compound is are applied at a rate of application of 0.05 to 12 kg per hectare.

12. A method according to claim 11, wherein the rate of application is in the range from 0.5 to 8 kg per hectare.

13. A method according to claim 12, wherein the rate of application is in the range from 1 to 4 kg per hectare.

14. A method according to claim 9, wherein the treatment is carried out postemergence, but before ears and anthers have appeared.

15. A method according to claim 9, wherein treatment of the plants is carried out in the 5½-leaf stage.

16. A method according to claim 1 wherein the compound is applied to cultivated plants before the start of flowering, thereby increasing the number of inflorescences.

17. A method according to claim 16, wherein application of the compound is made to sunflowers, cotton, marrows, cucumbers, melons, cereals, or ornamentals.

18. A method according to claim 16, wherein the compound is applied at a rate of application in the range from 0.5 to 4 kg per hectare.

* * * * *